United States Patent
Rosen et al.

(10) Patent No.: US 6,562,300 B2
(45) Date of Patent: May 13, 2003

(54) COLLECTION ASSEMBLY

(75) Inventors: Steven M. Rosen, Mountain Lakes, NJ (US); Allison Peckham, Wayne, NJ (US); Alois Prais, Rutherford, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/392,471

(22) Filed: Sep. 9, 1999

(65) Prior Publication Data

US 2002/0141904 A1 Oct. 3, 2002

Related U.S. Application Data

(60) Provisional application No. 60/143,215, filed on Jul. 9, 1999.

(51) Int. Cl.⁷ .............................. B01L 3/14; B65D 41/50
(52) U.S. Cl. ...................... 422/102; 215/211; 215/247; 215/320; 215/321; 215/354; 422/99
(58) Field of Search .................. 422/99, 102; 600/573, 600/577; 215/211, 214, 216, 217, 223, 224, 228, 247, 320, 321, 353, 354, 355, 318; 220/301, 302

(56) References Cited

U.S. PATENT DOCUMENTS

| | | | |
|---|---|---|---|
| 3,978,859 A | 9/1976 | Goodenough et al. | |
| 4,204,606 A | 5/1980 | Micheli | |
| 4,542,833 A | 9/1985 | DeVaughn | |
| 4,632,673 A | 12/1986 | Tiitola et al. | |
| 5,224,515 A | 7/1993 | Foster et al. | |
| 5,247,015 A | 9/1993 | Bayan | |
| 5,288,466 A | 2/1994 | Burns | |
| 5,306,270 A | 4/1994 | Macartney et al. | |
| 5,384,096 A | 1/1995 | Burns | |
| D357,985 S | 5/1995 | Burns | |
| 5,458,854 A | 10/1995 | Burns | |
| 5,494,170 A * | 2/1996 | Burns | 215/247 |
| 5,632,396 A * | 5/1997 | Burns | 215/247 |
| 5,738,233 A | 4/1998 | Burns | |
| 5,779,074 A | 7/1998 | Burns | |

FOREIGN PATENT DOCUMENTS

| | | |
|---|---|---|
| EP | 0 445 707 A2 | 9/1991 |
| EP | 0454493 A2 | 10/1991 |
| EP | 0903107 A1 | 3/1999 |
| JP | 10-201742 | 8/1998 |
| WO | WO89/02399 | 3/1989 |

* cited by examiner

Primary Examiner—John Kim
(74) Attorney, Agent, or Firm—Nanette S. Thomas, Esq.; Scott J. Rittman, Esq.

(57) ABSTRACT

The present invention is a collection assembly comprising a container, a cap assembly removably and sealably secured to the container whereby access to the interior of the container can be made with a piercing element without removing the cap assembly from the container. The cap assembly includes a cap body and a membrane like septum supported by the cap body. The septum provides for a pierceable element to have access to the interior of the container. The membrane is a thermoplastic elastomer and is self-sealing upon removal of the piercing element.

4 Claims, 5 Drawing Sheets

COLLECTION ASSEMBLY

This application claims the benefit of U.S. Provisional Application No. 60/143,215 filing date Jul. 9, 1999.

BACKGROUND OF THE INVENTION

1. Field of the Invention

The present invention relates to a collection assembly and more particularly to a microcollection container and cap assembly suitable for collecting small quantities of a specimen such as blood from a patient, that provides access to the interior of the container without the need for removing the cap from the assembly and for maintaining a specimen in secure fashion for subsequent testing.

2. Description of Related Art

Analytical instrumentation has made it possible to carry out a variety of hemological diagnostic procedures on very small quantities of blood. The blood may be collected from a small puncture placed in a patient's finger or ear lobe. The blood is collected in a microcollection container. Once the small quantities of blood are collected, the container is sealably covered by a cap.

In order for a laboratory technician to conduct tests on the blood sample which is collected in the container, the cap must be removed from the container so as to provide access to the blood sample. In the alternative, the entire contents of the container may be transferred from the container to an instrument compatible sample holder in order for laboratory analysis to take place.

Therefore, there is a need for a microcollection container that is (i) compatible with instruments for laboratory analysis whereby the specimen does not have to be transferred out of the container for analysis to be conducted; (ii) provides a resealable portion for easy access into the container by a needle or probe that also prevents specimen leakage out of the container; (iii) maintains a specimen in secure fashion; and (iv) prevents contamination to the specimen and to the user.

SUMMARY OF THE INVENTION

The present invention is a collection assembly comprising a container and a cap.

The container includes an open end, a closed end and a cylindrical wall therebetween which preferably comprises the interior of the container for accommodating the specimen.

Desirably, the cap comprises a cap body removably sealably secured to the open end of the container. The cap body supports a membrane for providing reseable access to the interior of the container. The membrane is formed of a material which is capable of being pierced and resealed on a repetitive basis with a needle or instrument probe. Most preferably, the membrane is formed of a thermoplastic elastomer. Such thermoplastic elastomers include isoprene propylene, such as MONOPRENE (a trademark of QST, Inc.) sold by QST, Inc., St. Albans, Vt.

Preferably, the membrane is disc-shaped having a concave surface facing away from the container interior which assists in resealing of the membrane. The thermoplastic elastomer allows for the resealing of the pierced membrane in a manner which prevents specimen leakage therethrough even when the collection assembly is held in an inverted position.

Preferably, the cap body includes a top portion, a bottom portion, a cylindrical sidewall extending from the top portion to the bottom portion having an inner surface and an outer surface, an access passageway at the top portion and a membrane supported across the passageway.

The cap body may further include a depending annular skirt extending into the interior of the container from the top portion and defining an annular region with the cylindrical sidewall. The open end of the container is accommodated within the annular region. The depending skirt includes an access passageway, with the membrane being supported across the passageway.

Preferably, the membrane and the cap body may be co-injection molded or insert molded.

An advantage of the present invention is that it facilitates direct access to a sample for diagnostic instrumentation systems and enables microcollection tube compatability with diagnostic instrumentation by providing features such as pierceability and self-resealing of the cap.

Still another advantage of the present invention is that the self-sealing pierceable cap permits mixing of the specimen in the container without transferring the specimen to another container and providing for direct access to the specimen via the self-sealing pierceable cap by diagnostic instrumentation.

Most notably, is that the present invention permits a specimen to be accessed through the top of the cap without removing the cap from the container, thereby providing minimal exposure of the specimen to the user.

In addition, the present invention permits the assembly to be directly used on instrumentation similar to that used for evacuated collection assemblies.

Advantages of the membrane of the present invention include that: (i) it can be pierced and resealed many times; (ii) it requires less than 2 lb. force for a piercing element to pierce it; and (iii) the concave shape aids in the ability of the membrane to seal properly after the piercing element is removed.

DETAILED DESCRIPTION

Figure 1:
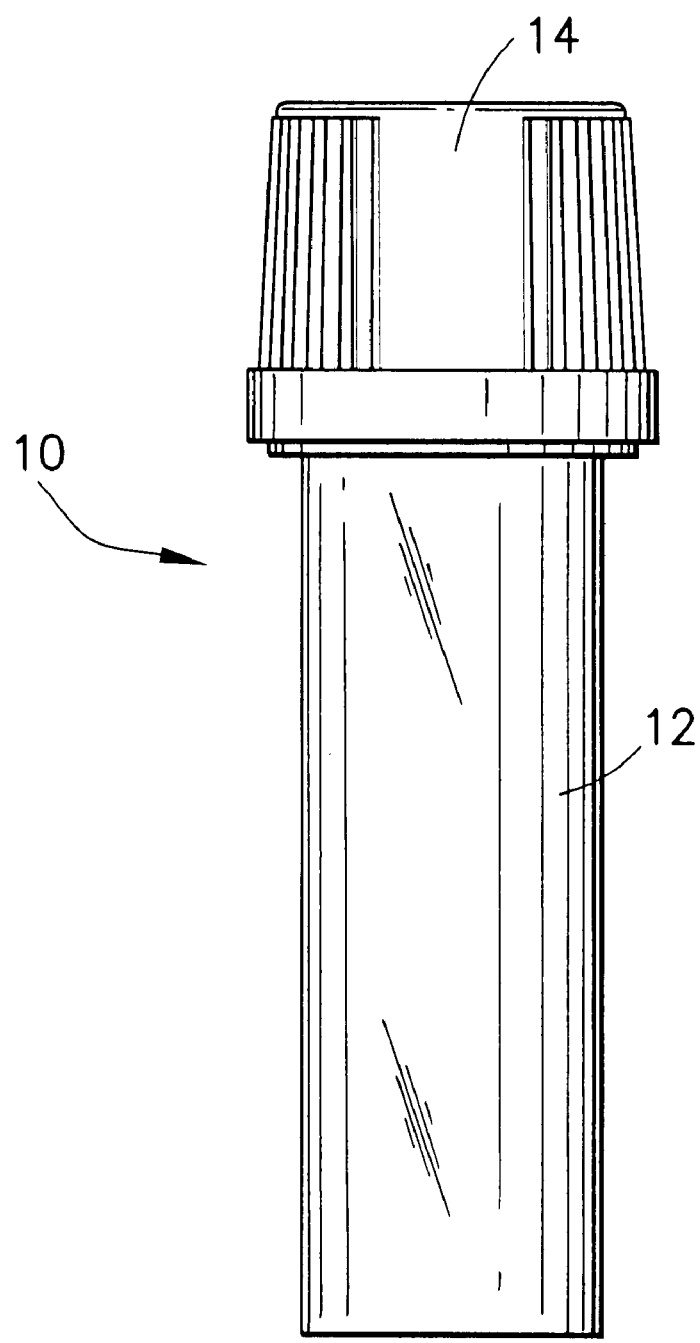
FIG. 1 is a front plan view of the collection assembly of the present invention.
Figure 2:
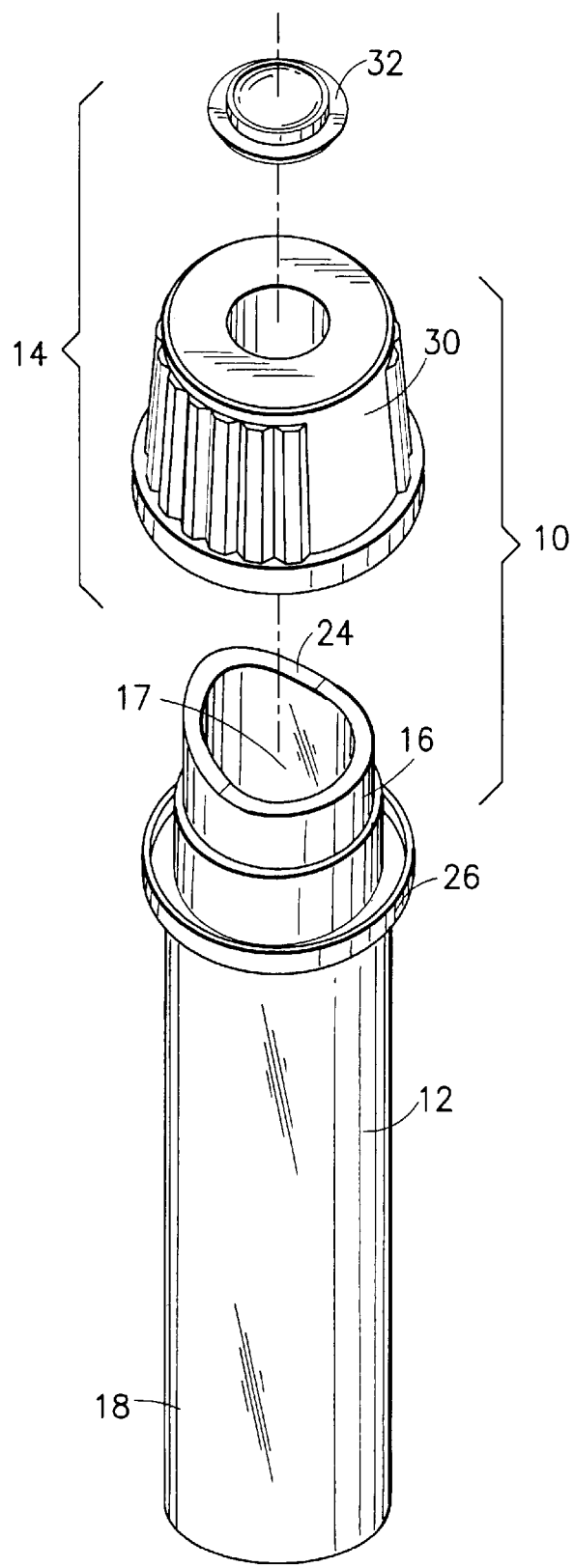
FIG. 2 is a perspective view of the collection assembly of FIG. 1 illustrating the container, the cap and the membrane.
Figure 3:
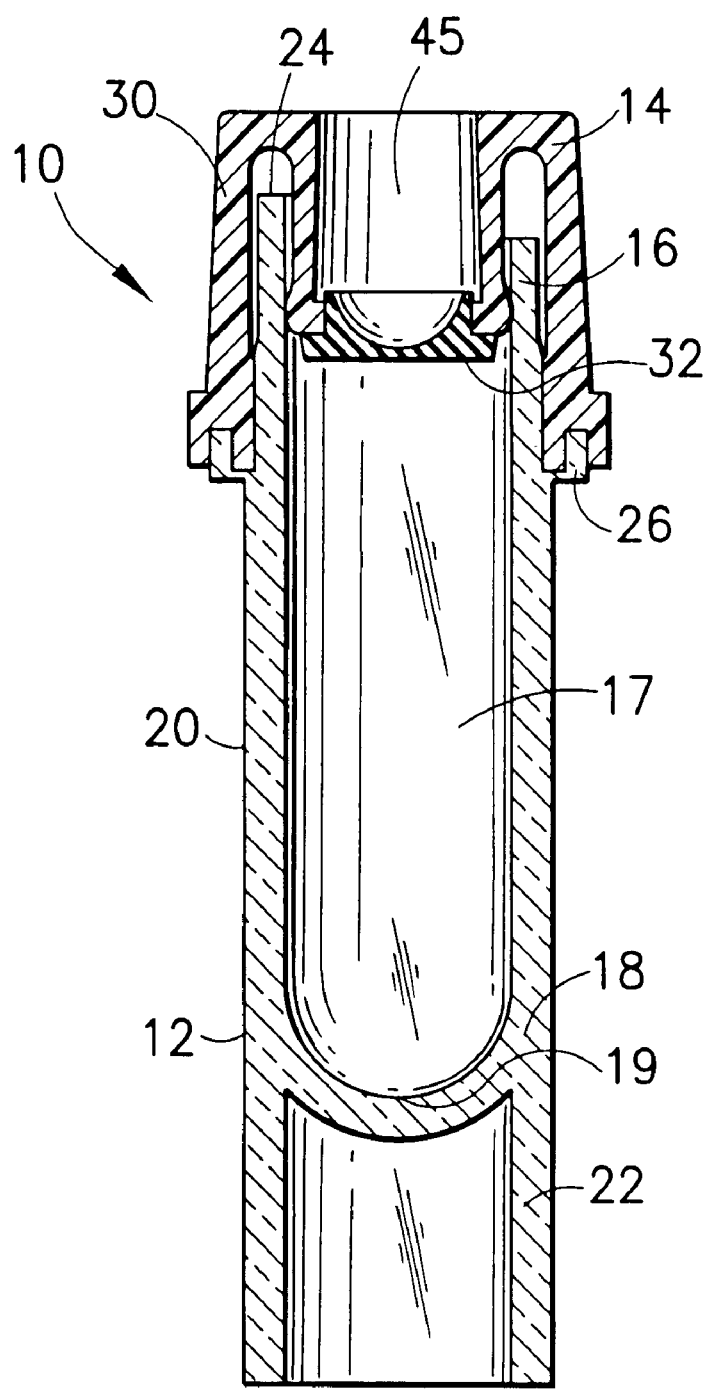
FIG. 3 is a cross sectional view of the collection assembly of FIG. 1.

Referring to the drawings in which like reference characters refer to like parts throughout the several views thereof, FIGS. 1–3 illustrate the collection assembly 10 of the present invention.

Collection assembly 10 includes a container 12 and a cap assembly 14. Cap assembly 14 may be removably secured to the container.

Container 12 is an elongate member having an open upper end 16, a lower end 18 including a rounded closed bottom end 19 and a cylindrical wall 20 extending therebetween. The cylindrical wall 20 defines an interior 17 internally thereof for accommodating a specimen such as a blood specimen. The cylindrical wall 20 extends beyond the rounded closed bottom 19 to form an annular extension 22 which permits container 12 to stand upright on a flat surface.

As shown in FIG. 2, open upper end 16 of container 12 includes a beveled distal rim 24 for facilitating collection of a blood sample. The upper end 16 of tube 12 further includes a radially outwardly extending cap seating flange 26 which provides for the removable sealable attachment of cap assembly 14 on upper end 16 of container 12. Once a specimen, such as blood is collected in interior 17 of the container, the container may be sealingly closed by cap assembly 14.

Figure 4:
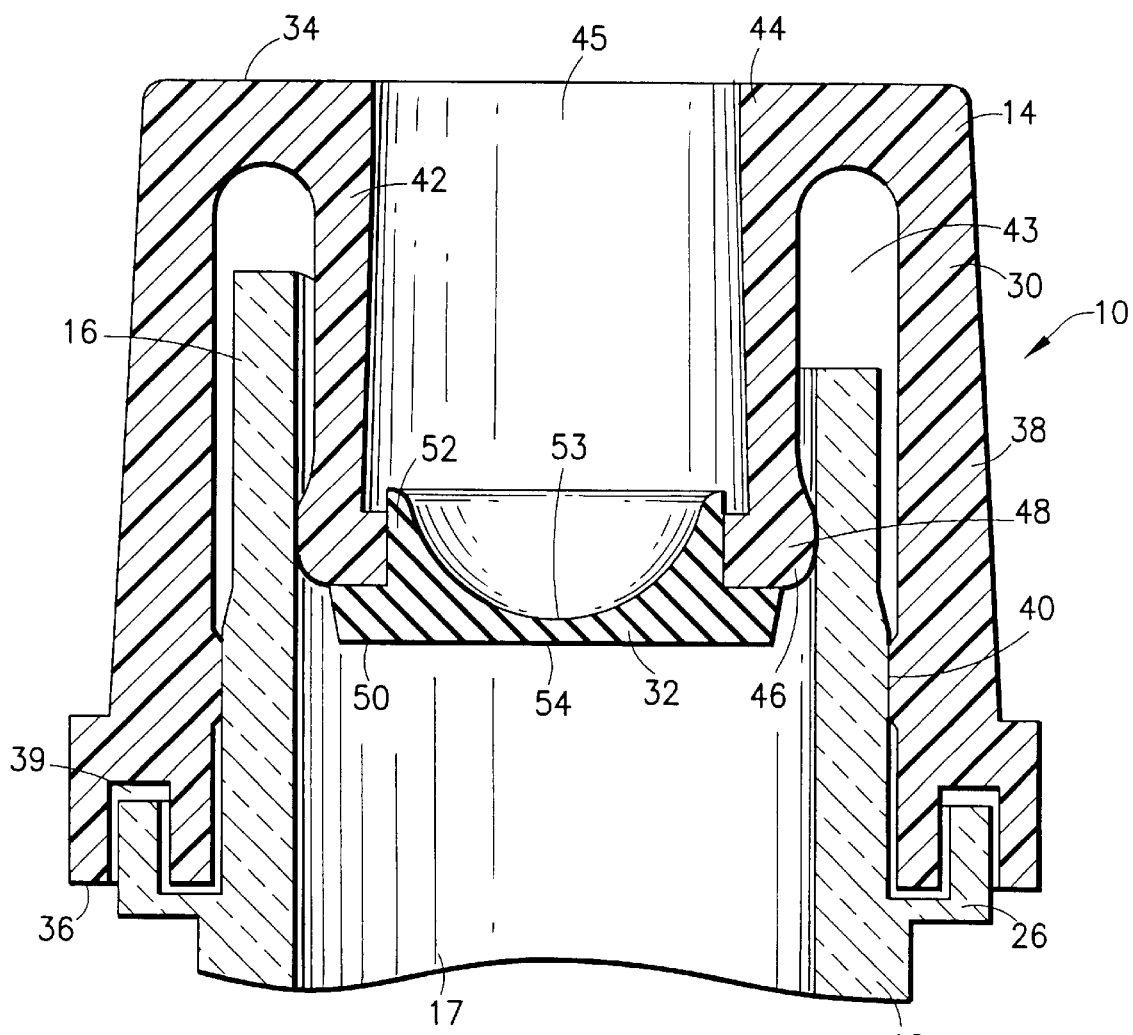
FIG. 4 is a side elevational view, partially in section of the collection assembly of FIG. 3.

Referring to FIG. 4, cap assembly 14 includes a cap body 30 and a sealable septum 32 supported by cap body 30. Cap body 30 is preferably an integrally formed molded plastic member generally in the shape of an inverted cup. The cap includes a flat upper surface 34, an opposed open lower surface 36 and a cylindrical sidewall 38 extending therebetween. The distal end of cylindrical sidewall 38 adjacent open lower surface 36 defines an annular groove 39 for accommodating cap seating flange 26 of the container. Cylindrical side wall 38 includes a plurality of inwardly directed protrusions 40 which engage an exterior surface of cylindrical wall 20 of the container about open upper end 16 to provide sealed engagement between cap body 30 and container 12.

Cap body 30 further includes a centrally located depending annular skirt 42 extending from flat upper surface 34. Annular skirt 42 and cylindrical side wall 38 form an open ended annular recess 43 therebetween for accommodating upper end 16 of container 12. Annular skirt 42 includes an open upper extent 44, an opposed open lower extent 46 extending into interior 17 of the container and a central passageway 45 therebetween which provides access through cap body 30 and into interior 17 of container 12. Lower extent 46 of annular skirt 42 includes an outwardly directed annular rib 48 which is engageable with an inner surface of cylindrical wall 20 adjacent open upper end 16 of container 12 to facilitate sealing of cap body 30 with container 12.

Cap body 30 further supports septum 32 at the lower extent 46 of annular skirt 42. Septum 32 is a disc-like membrane formed of a thermoplastic elastomer. As shown in FIG. 4, septum 32 includes a planar portion 50 and an upwardly extending annular ridge 52. Annular ridge 52 has a diameter which allows it to be force fitted within open lower extent 46 of annular skirt 42 and retained in sealed engagement. Planar portion 50 of septum 32 faces towards the interior of container 12. Annular ridge 52 defines a concave surface 53 in opposition to planar portion 50. Septum 32 defines a centrally located portion 54 having a thickness of about 0.028 inches. Portion 54 allows the septum to be easily pierced by a cannula or probe used to extract a liquid sample from interior 17 of container 12 with about 2 pounds of force.

In use, a liquid sample is collected in container 12 and then cap assembly 14 is sealably secured to the open upper end of the container.

Figure 5:
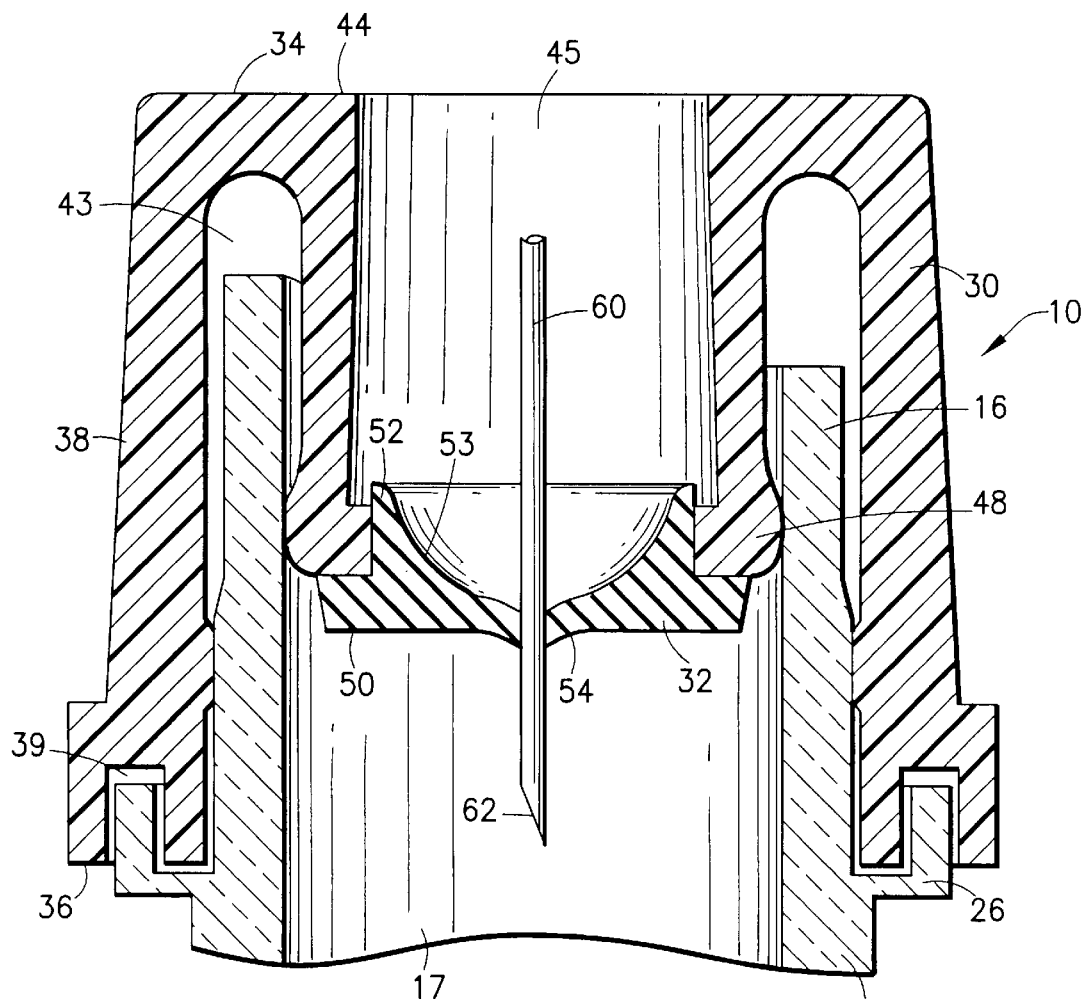
FIG. 5 illustrates the collection assembly of FIG. 4, with a probe extending thereinto.

As shown in FIG. 5, a sample probe or cannula 60 may be inserted into container 12 by inserting cannula 60 through passageway 45 of cap body 30. The distal tip 62 of cannula 60 may then pierce through septum 32 at portion 54. Since the material of septum 32 is a soft thermoplastic elastomer, septum 32 is easily pierced by low insertion forces. Therefore, for a relatively wide instrument probe having a diameter of about 0.0625 inches, portion 54 of septum 32 may be pierced by a force of less than 2 pounds.

Insertion of cannula 60 continues until it reaches the sample in interior 17 of container 12 and then collects a portion of the sample. Cannula 60 is then removed by withdrawing it back through passageway 45. Upon withdrawing cannula 60 from septum 32, the thermoplastic elastomer septum self-seals. In addition, concave surface 50 facing in opposition thereto helps reseal a hole placed in septum 32 by cannula 60. The septum shape defines a concave surface in the direction of cannula withdrawal. The compressive forces exerted by such a shape assist in resealing of any hole placed in septum 32 as cannula 60 is withdrawn from the container. Thus, the particular configuration of septum 32 as well as the material from which it is formed permits the septum to reseal after multiple puncture sites have been placed therein. The liquid sample in container 12 can therefore be repeatedly sampled with the septum self-sealing upon each sample extraction.

The collection assembly of the invention may be made of a molded thermoplastic material so that the specimen collected may be readily viewed. Representative materials include, for example, polyethylene, polypropylene and polyvinyl chloride. The collection container may incorporate a hydrophilic material or a silicon, or a texture may be applied to the internal surface thereof for enhancing the flow and mixing of blood introduced into the container.

Although it is within the purview of the invention to provide caps which are colored to defined specific forms of fluid collection containers containing materials for one reason or another or for defining the kind of examination to be conducted on the specimen collected, transparent caps may be provided. Also, it should be noted that the dimensions of the container are such as to provide space for labeling which may be important for identifying the collected specimens.

What is claimed is:

1. A specimen collection assembly comprising:
    an elongate specimen collection tube having an open end, a closed end and a cylindrical wall therebetween defining a tube interior for accommodating said specimen; and;
    a cap assembly having a cap body removably sealably secured to said open end of said tube, said cap body comprising an upper surface, an opposed lower surface, and a cylindrical sidewall therebetween, with a depending annular skirt extending from said upper surface of said cap body,
    wherein said cylindrical side wall and said annular skirt define an annular region therebetween for accommodating said open end of said tube,
    wherein said annular skirt comprises an elongate cylindrical skirt wall having an upper end and a lower end, with an access passageway through said cap body being defined between said upper end and said lower end, said lower end of said skirt wall extending into the tube interior, and
    wherein said cap body further comprises a septum supported across said lower end of said skirt wall, the septum formed of a thermoplastic elastomer and being self-sealing upon probe removal, and having a flat surface and an opposed concave surface facing away from the tube interior.

2. The specimen collection assembly of claim 1, whereby said cap body and said septum are co-injection molded.

3. A cap assembly for sealably covering an open ended specimen collection container comprising:
    a cap body being formed of rigid material for removable securement over said open end of said container,
    a pierceable septum supported by said cap body for providing probe pierceable access to said container through said cap, wherein said cap body comprises an upper surface, an opposed lower surface, and a cylindrical sidewall therebetween, with a depending annular skirt extending from said upper surface of said cap body, wherein said cylindrical sidewall and said annular skirt define an annular region therebetween, wherein said annular skirt comprises an elongate cylindrical skirt wall having an upper end and a lower end, with an access passageway through said cap body being defined between said upper end and said lower end, and wherein said cap body further comprises a septum supported across said lower end of said skirt wall, the septum formed of a thermoplastic elastomeric membrane capable of self-sealing upon probe removal, and having a flat surface and an opposed concave surface facing said upper surface.

4. The cap assembly of claim 3, whereby said cap body and said pierceable septum are co-injection molded.

* * * * *